United States Patent

Huang et al.

(10) Patent No.: US 10,003,032 B2
(45) Date of Patent: Jun. 19, 2018

(54) ORGANIC ELECTROLUMINESCENT MATERIALS CONTAINING BENZIMIDAZOLE AND ORGANIC ELECTROLUMINESCENT DEVICE BY USING THE SAME

(71) Applicant: Yuan Ze University, Chung-Li (TW)

(72) Inventors: Jau-Jiun Huang, Chung-Li (TW);
Man-Kit Leung, Chung-Li (TW);
Tien-Lung Chiu, Chung-Li (TW);
Jiun-Haw Lee, Chung-Li (TW);
Yu-Hsiang Hung, Chung-Li (TW);
Lik-Ka Yun, Chung-Li (TW)

(73) Assignee: YUAN ZE UNIVERSITY, Chung-Li (TW)

( * ) Notice: Subject to any disclaimer, the term of this patent is extended or adjusted under 35 U.S.C. 154(b) by 162 days.

(21) Appl. No.: 14/983,850

(22) Filed: Dec. 30, 2015

(65) Prior Publication Data

US 2017/0162793 A1  Jun. 8, 2017

(30) Foreign Application Priority Data

Dec. 3, 2015  (TW) .............................. 104140605 A

(51) Int. Cl.
| | | |
|---|---|---|
| H01L 51/00 | (2006.01) | |
| C07D 403/10 | (2006.01) | |
| C07D 403/14 | (2006.01) | |
| C09K 11/02 | (2006.01) | |
| C09K 11/06 | (2006.01) | |
| H01L 51/50 | (2006.01) | |

(52) U.S. Cl.
CPC ........ *H01L 51/0072* (2013.01); *C07D 403/10* (2013.01); *C07D 403/14* (2013.01); *C09K 11/025* (2013.01); *C09K 11/06* (2013.01); *H01L 51/0085* (2013.01); *C09K 2211/1007* (2013.01); *C09K 2211/1029* (2013.01); *C09K 2211/185* (2013.01); *H01L 51/5016* (2013.01)

(58) Field of Classification Search
CPC ............. H01L 51/0072; H01L 51/0085; H01L 51/5016; C07D 403/10; C07D 403/14; C09K 11/025; C09K 11/06
See application file for complete search history.

(56) References Cited

U.S. PATENT DOCUMENTS

| | | | | |
|---|---|---|---|---|
| 2004/0146745 A1* | 7/2004 | Ise | ........................ | C07D 471/04 428/690 |
| 2013/0075705 A1* | 3/2013 | Takasu | .................. | C07D 403/14 257/40 |
| 2016/0133844 A1* | 5/2016 | Kim | .................... | H01L 51/0054 257/40 |

FOREIGN PATENT DOCUMENTS

| | | |
|---|---|---|
| CN | 103524497 A | 1/2014 |
| TW | 201533039 A | 9/2015 |

OTHER PUBLICATIONS

Atul Chaskar, "Bipolar Host Materials: A Chemical Approach for Highly Efficient Electrophosphorescent Devices", Adv. Mater, 2011, pp. 3876-3895.

* cited by examiner

*Primary Examiner* — Anca Eoff
(74) *Attorney, Agent, or Firm* — Muncy, Geissler, Olds & Lowe, P.C.

(57) ABSTRACT

An organic electroluminescent material is shown in formula (1),

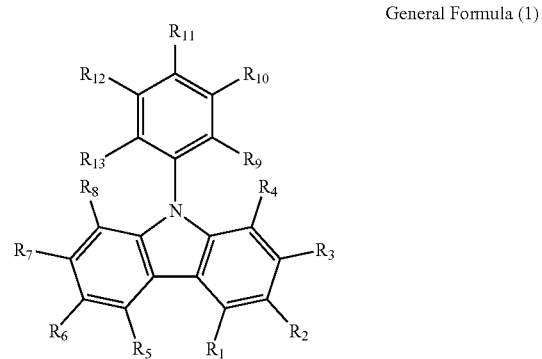

General Formula (1)

Wherein $R_9$ or/and $R_{13}$ is/are benzimidazole derivative(s), benzimidazole derivative is shown in formula (3)

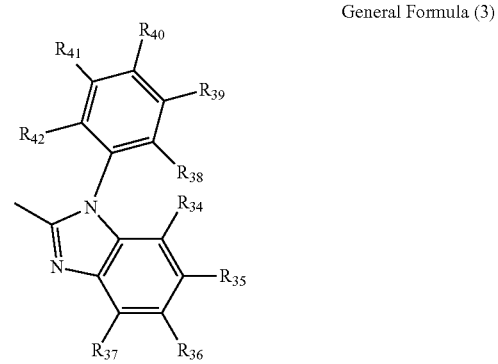

General Formula (3)

Wherein the rest of functional groups are independently selected from one of hydrogen atom, fluorine atom, cyano group, alkyl group, cycloalkyl group, alkoxy group, thioalkyl group, silyl group and alkenyl group.

10 Claims, 1 Drawing Sheet

ORGANIC ELECTROLUMINESCENT MATERIALS CONTAINING BENZIMIDAZOLE AND ORGANIC ELECTROLUMINESCENT DEVICE BY USING THE SAME

CROSS REFERENCE TO RELATED APPLICATIONS

This Non-provisional application claims priority under 35 U.S.C. § 119(a) on Patent Application No(s). 104140605 filed in Taiwan, Republic of China on Dec. 3, 2015, the entire contents of which are hereby incorporated by reference.

BACKGROUND OF THE INVENTION

Technical Field

The present invention relates to an organic electroluminescent material and an organic electroluminescent device and, in particular, to an organic electroluminescent material containing benzimidazole and an organic electroluminescent device.

Related Art

With the advances in electronic technology, a light weight and high efficiency flat display device has been developed. An organic electroluminescent display possibly becomes the mainstream of the next generation flat panel display device due to its advantages of self-luminosity, no restriction on viewing angle, power conservation, simple manufacturing process, low cost, high response speed, full color and so on.

In general, an organic electroluminescent device includes an anode, an organic luminescent layer and a cathode. When a direct current is provided for the organic electroluminescent device, electron holes and electrons flow into the organic luminescent layer respectively through the anode and the cathode. Charge carriers move and then recombine in the organic luminescent layer because of the potential difference caused by an applied electric field. The excitons generated by the recombination of the electrons and the electron holes may excite the luminescent molecules in the organic luminescent layer. The excited luminescent molecules then release the energy in the form of light.

Nowadays, organic electroluminescent displays usually adopt host-guest emitter systems. The organic luminescent layer disposed therein includes a host material and a guest material. Electron holes and electrons transmit to the host material to perform recombination and then generate energy. The guest material can be categorized into fluorescent material and phosphorescent material. Theoretically, the internal quantum efficiency can approach 100% by using appropriate phosphorescent materials. Therefore, the phosphorescent materials recently have become one of the most important developments in the field of organic electroluminescent materials.

In the development of blue host materials, the triplet energy gap of the host materials must be higher than or equal to that of the guest materials to avoid the energy lost caused by reverse energy transfer. The energy lost can result in low luminous efficiency (i.e., low current efficiency) and short emission lifetime. Therefore, it is necessary for the host materials to have greater triplet energy gap. In order to increase the triple energy gap of the blue host materials, much research has been focused on the single benzene ring with various ortho-substituted groups. In ortho-substitution with electron-transporting group (e.g., OXD or TAZ) and hole-transporting group (e.g., Cbz), a bipolar molecule is created by interrupted π-conjugated molecules due to steric hindrance.

Besides, the selection of organic electroluminescent material is not only based on the matching energy gap but also the high temperature of decomposition to avoid pyrolysis caused by high temperature and also avoid the resulted decreasing of stability.

Accordingly, the present invention is provided an organic electroluminescent material containing benzimidazole and an organic electroluminescent device which has high triplet energy gap and fine thermal stability.

SUMMARY OF THE INVENTION

In view of the foregoing objectives, the invention provides a series of organic electroluminescent materials containing benzimidazole and carbazole, and an organic electroluminescent device by using the same. The organic electroluminescent material has high triplet energy gap and fine thermal stability.

An organic electroluminescent material according to the present invention has a structure of the following General Formula (1).

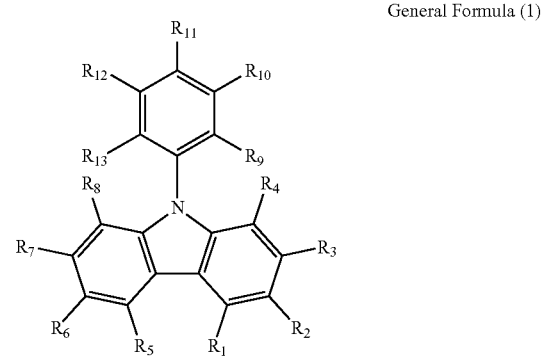

General Formula (1)

One or two of R9 and R13 are each independent benzimidazole derivatives which have the structures of the following General Formula (3).

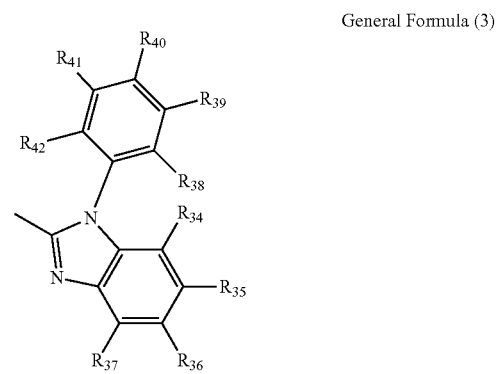

General Formula (3)

When R9 is the benzimidazole derivative, R1 to R8, R10 to R13 and R34 to R42 are each independently selected from the group consisting of a hydrogen atom, a fluorine atom, a cyano group, an alkyl group, a cycloalkyl group, an alkoxy group, a thioalkyl group, a silyl group, and an alkenyl group. When R13 is the benzimidazole derivative, R1 to R12 and R34 to R42 are each independently selected from the group consisting of a hydrogen atom, a fluorine atom, a cyano group, an alkyl group, a cycloalkyl group, an alkoxy group, a thioalkyl group, a silyl group, and an alkenyl group. When R9 and R13 are both the benzimidazole derivatives, R1 to R8, R10 to R12 and R34 to R42 are each independently selected from the group consisting of a hydrogen atom, a fluorine atom, a cyano group, an alkyl group, a cycloalkyl group, an alkoxy group, a thioalkyl group, a silyl group, and an alkenyl group.

In one embodiment, the alkyl group is selected from the group consisting of a substituted or unsubstituted straight-chain alkyl group with the carbon number of 1 to 6, and a substituted or unsubstituted branched-chain alkyl group with the carbon number of 1 to 6. The cycloalkyl group is a substituted or unsubstituted cycloalkyl group with the carbon number of 1 to 6. The alkoxy group is selected from the group consisting of a substituted or unsubstituted straight-chain alkoxy group with the carbon number of 1 to 6, and a substituted or unsubstituted branched-chain alkoxy group with the carbon number of 1 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 1 to 6. The silyl group is selected from the group consisting of a substituted or unsubstituted straight-chain silyl group with the carbon number of 1 to 6, and a substituted or unsubstituted branched-chain silyl group with the carbon number of 1 to 6. The alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

An organic electroluminescent material according to the present invention has a structure of the following General Formula (2).

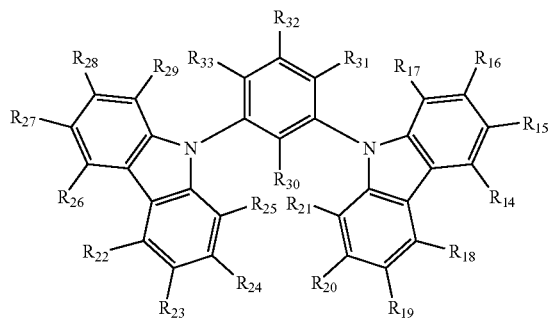

General Formula (2)

R30 is an independent benzimidazole derivative, and the benzimidazole derivative has the structure of the following General Formula (3).

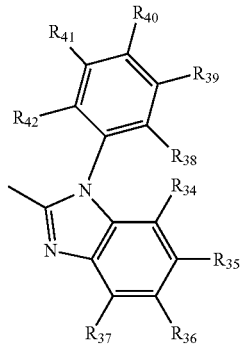

General Formula (3)

R14 to R29 and R31 to R42 are each independently selected from the group consisting of a hydrogen atom, a fluorine atom, a cyano group, an alkyl group, a cycloalkyl group, an alkoxy group, a thioalkyl group, a silyl group, and an alkenyl group.

In one embodiment, the alkyl group is selected from the group consisting of a substituted or unsubstituted straight-chain alkyl group with the carbon number of 1 to 6, and a substituted or unsubstituted branched-chain alkyl group with the carbon number of 1 to 6. The cycloalkyl group is a substituted or unsubstituted cycloalkyl group with the carbon number of 1 to 6. The alkoxy group is selected from the group consisting of a substituted or unsubstituted straight-chain alkoxy group with the carbon number of 1 to 6, and a substituted or unsubstituted branched-chain alkoxy group with the carbon number of 1 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 1 to 6. The silyl group is selected from the group consisting of a substituted or unsubstituted straight-chain silyl group with the carbon number of 1 to 6, and a substituted or unsubstituted branched-chain silyl group with the carbon number of 1 to 6. The alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

An organic electroluminescent device which is also provided includes a first electrode layer, a second electrode layer, and an organic luminescent unit. The organic luminescent unit is disposed between the first electrode layer and the second electrode layer. The organic luminescent unit has at least an organic luminescent material as shown in General Formula (1).

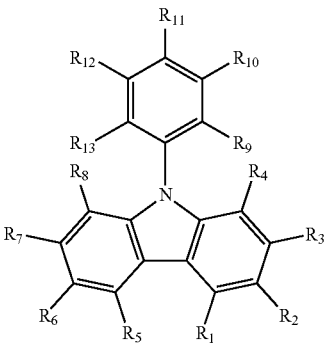

General Formula (1)

One or two R9 and R13 are each independent benzimidazole derivatives, and the benzimidazole derivatives have the structures of the following General Formula (3).

General Formula (3)

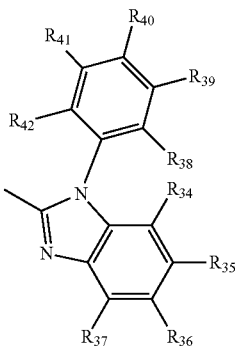

When R9 is the benzimidazole derivative, R1 to R8, R10 to R23 and R34 to R42 are each independently selected from the group consisting of a hydrogen atom, a fluorine atom, a cyano group, an alkyl group, a cycloalkyl group, an alkoxy group, a thioalkyl group, a silyl group, and an alkenyl group. When R13 is the benzimidazole derivative, R1 to R12 and R34 to R42 are each independently selected from the group consisting of a hydrogen atom, a fluorine atom, a cyano group, an alkyl group, a cycloalkyl group, an alkoxy group, a thioalkyl group, a silyl group, and an alkenyl group. When R9 and R13 are both the benzimidazole derivatives, R1 to R8, R10 to R12 and R34 to R42 are each independently selected from the group consisting of a hydrogen atom, a fluorine atom, a cyano group, an alkyl group, a cycloalkyl group, an alkoxy group, a thioalkyl group, a silyl group, and an alkenyl group.

In one embodiment, the alkyl group is selected from the group consisting of a substituted or unsubstituted straight-chain alkyl group with the carbon number of 1 to 6, and a substituted or unsubstituted branched-chain alkyl group with the carbon number of 1 to 6. The cycloalkyl group is a substituted or unsubstituted cycloalkyl group with the carbon number of 1 to 6. The alkoxy group is selected from the group consisting of a substituted or unsubstituted straight-chain alkoxy group with the carbon number of 1 to 6, and a substituted or unsubstituted branched-chain alkoxy group with the carbon number of 1 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 1 to 6. The silyl group is selected from the group consisting of a substituted or unsubstituted straight-chain silyl group with the carbon number of 1 to 6, and a substituted or unsubstituted branched-chain silyl group with the carbon number of 1 to 6. The alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

In one embodiment, the organic luminescent unit comprises an organic luminescent layer.

In one embodiment, the organic luminescent unit further comprises a hole transport layer and an electron transport layer, and the organic luminescent layer is disposed between the hole transport layer and the electron transport layer.

In one embodiment, the organic luminescent unit further comprises a hole transport layer, an electron blocking layer, an electron transport layer and an electron injection layer, and the electron blocking layer, the organic luminescent layer and the electron transport layer are sequentially disposed between the hole transport layer and the electron injection layer.

In one embodiment, the organic luminescent layer comprises a host material and a guest material. The host material is the organic electroluminescent layer and the guest material is a phosphorescent material.

In one embodiment, the content of host material in organic luminescent layer is between 60 vol % to 95 vol %.

In one embodiment, the content of guest material in organic luminescent layer is between 5 vol % to 40 vol %.

An organic electroluminescent device which is also provided includes a first electrode layer, a second electrode layer, and an organic luminescent unit. The organic luminescent unit disposed between the first electrode layer and the second electrode layer. The organic luminescent unit has at least an organic electroluminescent material as shown in General Formula (2).

General Formula (2)

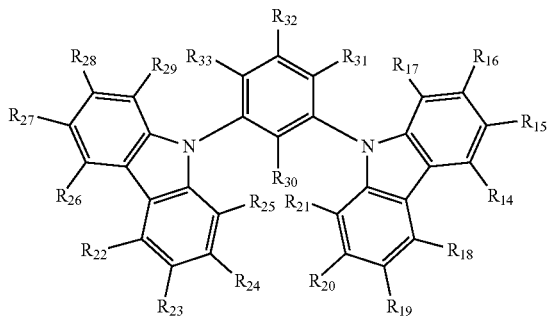

R30 is an independent benzimidazole derivative, and the benzimidazole derivative has the structures of the following General Formula (3).

General Formula (3)

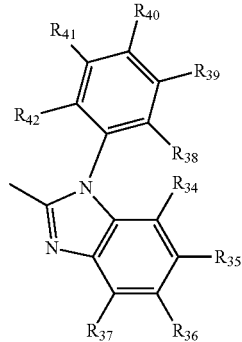

R14 to R29 and R31 to R42 are each independently selected from the group consisting of a hydrogen atom, a fluorine atom, a cyano group, an alkyl group, a cycloalkyl group, an alkoxy group, a thioalkyl group, a silyl group, and an alkenyl group.

In one embodiment, the alkyl group is selected from the group consisting of a substituted or unsubstituted straight-chain alkyl group with the carbon number of 1 to 6, and a substituted or unsubstituted branched-chain alkyl group with the carbon number of 1 to 6. The cycloalkyl group is a substituted or unsubstituted cycloalkyl group with the carbon number of 1 to 6. The alkoxy group is selected from the group consisting of a substituted or unsubstituted straight-chain alkoxy group with the carbon number of 1 to 6, and a substituted or unsubstituted branched-chain alkoxy group with the carbon number of 1 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 1 to 6. The silyl group is selected from the group consisting of a substituted or unsubstituted straight-chain silyl group with the carbon number of 1 to 6, and a substituted or unsubstituted branched-chain silyl group with the carbon number of 1 to 6. The alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

In one embodiment, the organic luminescent unit comprises an organic luminescent layer.

In one embodiment, the organic luminescent unit further comprises a hole transport layer and an electron transport layer and the organic luminescent layer is disposed between the hole transport layer and the electron transport layer.

In one embodiment, the organic electroluminescent unit further comprises a hole transport layer, an electron blocking layer, an electron transport layer and an electron injection layer, and the electron blocking layer, the organic luminescent layer and the electron transport layer are sequentially disposed between the hole transport layer and the electron injection layer.

In one embodiment, the organic luminescent layer comprises a host material and a guest material, and the host material is the organic electroluminescent material and the guest material is a phosphorescent material.

In one embodiment, the content of the host material in the organic luminescent layer is between 60 vol % to 95 vol %.

In one embodiment, the content of the guest material in the organic luminescent layer is between 5 vol % to 40 vol %.

As mentioned above, the organic electroluminescent material containing benzimidazole and the organic electroluminescent device according to the present invention is based on the structure of N-phenylcarbazole (NPC) and 1,3-Bis (N-carbazolyl)benzene (mCP) and in ortho-substitution with various number of electron-transporting benzimidazoles. Accordingly, the host materials with bipolar property, such as o-CbzBz, o-CbzDiBz and o-DiCbzBz, are formed. In the present invention, it utilizes the benzimidazole group to be electron-transporting group and the carbazole group to be hole-transporting group to synthesize a series of phosphorescent bipolar host materials. Therefore, such phosphorescent bipolar host materials and the organic light-emitting diode comprising such material will have high luminous efficiency.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

Figure 1:
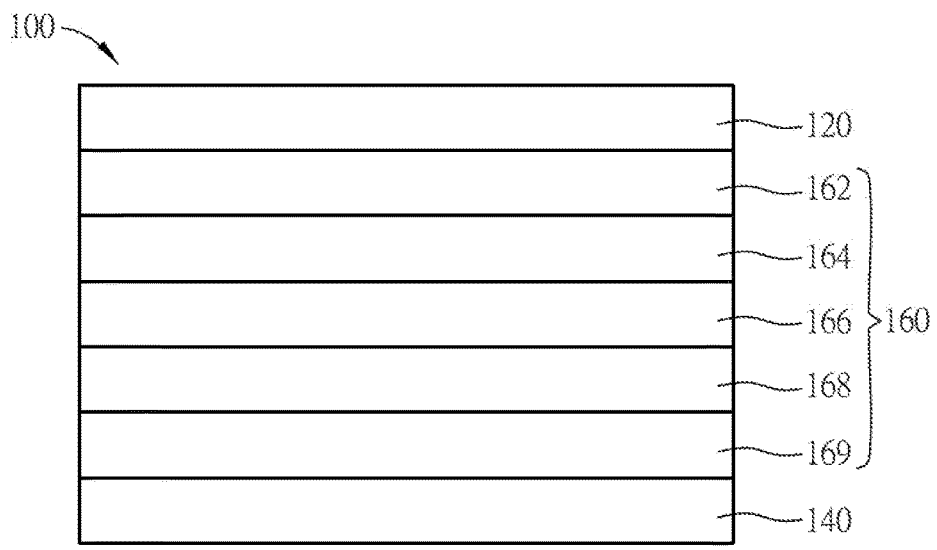
FIG. 1 is a schematic diagram of an organic electroluminescent device of the third embodiment according to the invention.

The embodiments of the invention will be apparent from the following detailed description, which proceeds with reference to the accompanying drawings, wherein the same references relate to the same elements.

Organic Electroluminescent Material

An organic electroluminescent material according to the first embodiment of the present invention has a structure of the following General Formula (1).

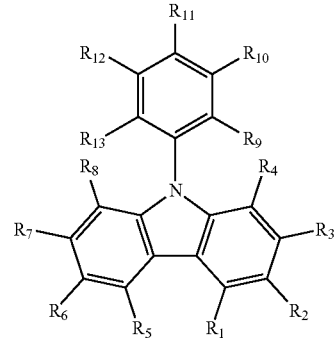

General Formula (1)

One or two of R9 and R13 are each independent benzimidazole derivatives which have the structures of the following General Formula (3).

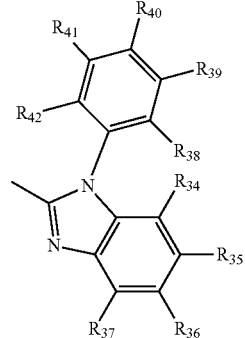

General Formula (3)

Namely in the embodiment, when R9 is the benzimidazole derivative, R1 to R8, R10 to R13 and R34 to R42 are each independently selected from the group consisting of a hydrogen atom, a fluorine atom, a cyano group, an alkyl group, a cycloalkyl group, an alkoxy group, a thioalkyl group, a silyl group, and an alkenyl group. When R13 is the benzimidazole derivative, R1 to R12 and R34 to R42 are each independently selected from the group consisting of a hydrogen atom, a fluorine atom, a cyano group, an alkyl group, a cycloalkyl group, an alkoxy group, a thioalkyl group, a silyl group, and an alkenyl group. When R9 and R13 are both the benzimidazole derivatives, R1 to R8, R10 to R12 and R34 to R42 are each independently selected from the group consisting of a hydrogen atom, a fluorine atom, a cyano group, an alkyl group, a cycloalkyl group, an alkoxy group, a thioalkyl group, a silyl group, and an alkenyl group.

In the embodiment, the alkyl group is selected from the group consisting of a substituted or unsubstituted straight-chain alkyl group with the carbon number of 1 to 6, and a substituted or unsubstituted branched-chain alkyl group with the carbon number of 1 to 6. The cycloalkyl group is a substituted or unsubstituted cycloalkyl group with the carbon number of 1 to 6. The alkoxy group is selected from the group consisting of a substituted or unsubstituted straight-chain alkoxy group with the carbon number of 1 to 6, and a substituted or unsubstituted branched-chain alkoxy group with the carbon number of 1 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 1 to 6. The silyl group is selected from the group consisting of a substituted or unsubstituted straight-chain silyl group with the carbon number of 1 to 6, and a substituted or unsubstituted branched-chain silyl group with the carbon number of 1 to 6. The alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

The organic electroluminescent material of General Formula (1) according to the embodiment can be the host material of the organic luminescent layer in an organic electroluminescent device. A preferred example is the compound of Chemical Formula (1), o-CbzBz, where R9 is a benzimidazole group, and R1 to R8, R10 to R13 and R34 to R42 are all independent hydrogen atoms.

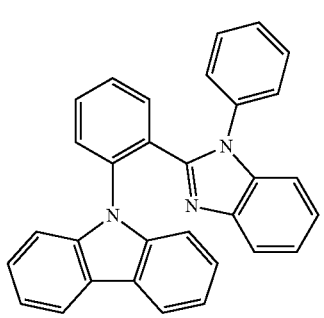

Chemical Formula (1)

Alternatively, another preferred example is the compound of Chemical Formula (2), o-CbzDiBz, where R9 and R13 are both independent benzimidazole groups, and R1 to R8, R10 to R12 and R34 to R42 are all independent hydrogen atoms.

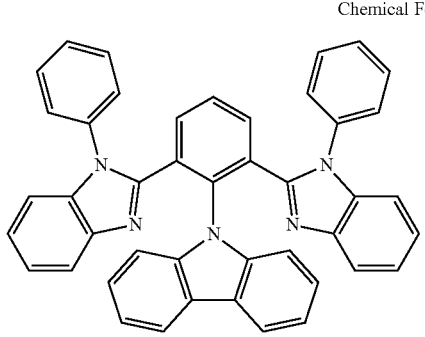

Chemical Formula (2)

An organic electroluminescent material according to the second embodiment of the present invention has a structure of the following General Formula (2).

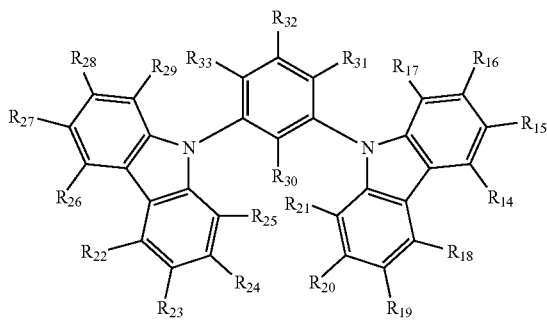

General Formula (2)

Namely in the embodiment, R30 is an independent benzimidazole derivative, and the benzimidazole derivative has the structure of the following General Formula (3).

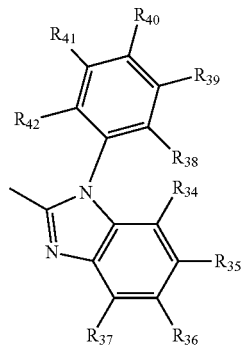

General Formula (3)

R14 to R29 and R31 to R42 are each independently selected from the group consisting of a hydrogen atom, a fluorine atom, a cyano group, an alkyl group, a cycloalkyl group, an alkoxy group, a thioalkyl group, a silyl group, and an alkenyl group.

In the embodiment, the alkyl group is selected from the group consisting of a substituted or unsubstituted straight-chain alkyl group with the carbon number of 1 to 6, and a substituted or unsubstituted branched-chain alkyl group with the carbon number of 1 to 6. The cycloalkyl group is a substituted or unsubstituted cycloalkyl group with the carbon number of 1 to 6. The alkoxy group is selected from the group consisting of a substituted or unsubstituted straight-chain alkoxy group with the carbon number of 1 to 6, and a substituted or unsubstituted branched-chain alkoxy group with the carbon number of 1 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 1 to 6. The silyl group is selected from the group consisting of a substituted or unsubstituted straight-chain silyl group with the carbon number of 1 to 6, and a substituted or unsubstituted branched-chain silyl group with the carbon number of 1 to 6. The alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

The organic electroluminescent material of General Formula (2) according to the embodiment can also be the host material of the organic luminescent layer in an organic electroluminescent device. A preferred example is the compound of Chemical Formula (3), o-DiCbzBz, where R14 to R29 and R31 to R42 are all independent hydrogen atoms.

Chemical Formula (3)

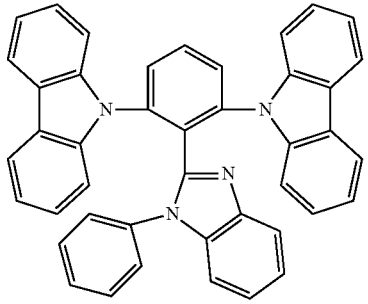

In the first and second embodiment, the benzimidazole derivative having the structure of General Formula (3) is functioned as an electron-transporting group and the carbazole group is functioned as a hole-transporting group. In addition, the carbazole group is undergone single ortho-substituted benzene ring modification and therefore a series of phosphorescent bipolar host materials is synthesized accordingly. Such phosphorescent bipolar host materials and the organic light-emitting diode comprising such materials will have high luminous efficiency. In other words, the host materials according to the above-mentioned embodiments comprise an electron-transporting group and a hole-transporting group in single molecule and has a characteristic of bipolar carrier-transporting.

Furthermore, the guest materials for use with the host materials described in the first and the second embodiment may be any suitable luminescent materials applied to the organic luminescent layer of the organic electroluminescent device, for example but not limited to, Ir(2-phq)$_3$, Ir(ppy)$_3$, and FIrpic, and their structures are respectively shown as the following Chemical Formula (4), Chemical Formula (5), and Chemical Formula (6).

Chemical Formula (4)

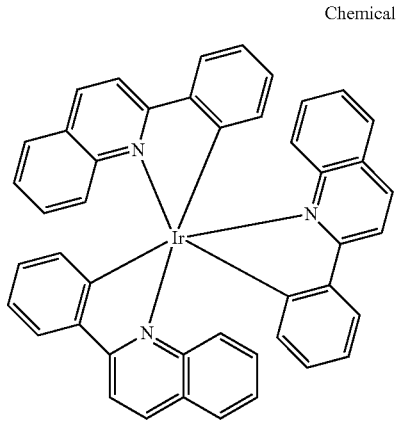

Chemical Formula (5)

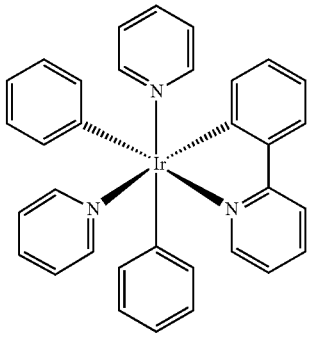

Chemical Formula (6)

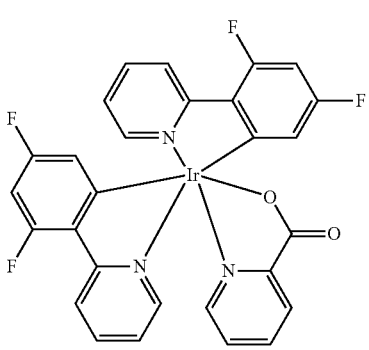

Moreover, the materials having the structures of General Formula (1) and General Formula (2), in addition to being applied in the organic luminescent layer, can also be applied in any layer of an organic electroluminescent unit, for example, a hole injection layer, hole transport layer, electron blocking layer, electron transport layer, or electron injection layer.

Organic Electroluminescent Device

Referring to FIG. 1, it is a schematic diagram of an organic electroluminescent device of the third embodiment according to the invention. The organic electroluminescent device 100 of the embodiment includes a first electrode layer 120, a second electrode layer 140, and an organic luminescent unit 160. In the embodiment, the first electrode layer 120 can be a transparent electrode material, such as indium tin oxide (ITO), and the second electrode layer 140 may be a metal, transparent conductive substance, or any other suitable conductive material. On the other hand, the first electrode layer 120 can be may be a metal, transparent conductive substance, or any other suitable conductive material, and the second electrode layer 140 may be a transparent electrode material. Overall, at least one of the first electrode layer 120 and the second electrode layer 140 of the embodiment is a transparent electrode material, so that the light emitted from the organic luminescent unit 23 may pass through the transparent electrode, thereby enabling the organic electroluminescent device 100 to emit light.

In addition, please also refer to FIG. 1, the organic luminescent unit 160 can comprise a hole transport layer 162, electron blocking layer 164, organic luminescent layer 166, electron transport layer 168, and electron injection layer 169. The electron blocking layer 164, the organic luminescent layer 166 and the electron transport layer 168 are sequentially disposed between the hole transport layer 162 and the electron injection layer 169.

The materials of the hole transport layer 162 may be 1,1-Bis[4-[N,N'-di(p-tolyl)amino]phenyl]cyclohexane (TAPC), N,N-bis-(1-naphthyl)-N,N-diphenyl-1,1-biphenyl-4,4-diamine (NPB), or N—N'-diphenyl-N—N'bis(3-methylphenyl)-[1-1'-biphenyl]-4-4'-diamine (TPD). Moreover, the thickness of the hole transport layer 162 of the embodiment is in the range of, for example, 0.1 nm to 100 nm. The hole transport layer 162 may facilitate the electron hole to be transported from the first electrode layer 120 to the organic luminescent layer 166 in order to increase the transport rate of the electron hole, and also to reduce the driving voltage of the organic electroluminescent device 100.

The materials of the electron blocking layer 164 may be N,N'-dicarbazolyl-3,5-benzene (mCP) or any other material with low electron affinity. In the embodiment, the thickness of the electron blocking layer 164 is in the range of, for example, 0.1 nm to 30 nm. The electron blocking layer 164 may further increase the transport rate of the electron hole from the hole transport layer 162 to the organic luminescent layer 166.

The thickness of the organic luminescent layer 166 of the embodiment is between 5 nm and 60 nm, the organic luminescent layer 166 includes the host material and the guest material, and the host material can be the above mentioned organic electroluminescent material which has a structure of the following General Formula (1).

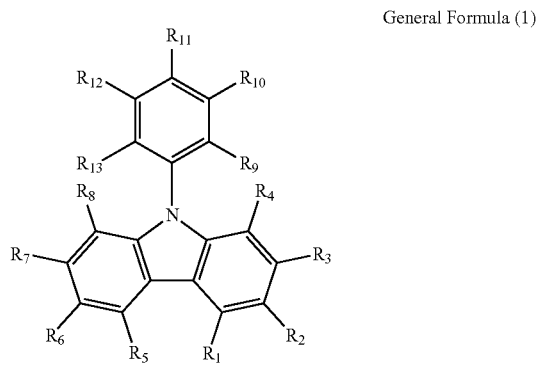

General Formula (1)

One or two of R9 and R13 are each independent benzimidazole derivatives which have the structures of the following General Formula (3).

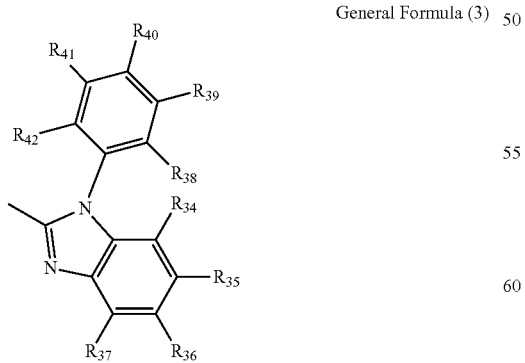

General Formula (3)

When R9 is the benzimidazole derivative, R1 to R8, R10 to R13 and R34 to R42 are each independently selected from the group consisting of a hydrogen atom, a fluorine atom, a cyano group, an alkyl group, a cycloalkyl group, an alkoxy group, a thioalkyl group, a silyl group, and an alkenyl group.

When R13 is the benzimidazole derivative, R1 to R12 and R34 to R42 are each independently selected from the group consisting of a hydrogen atom, a fluorine atom, a cyano group, an alkyl group, a cycloalkyl group, an alkoxy group, a thioalkyl group, a silyl group, and an alkenyl group.

When R9 and R13 are both the benzimidazole derivatives, R1 to R8, R10 to R12 and R34 to R42 are each independently selected from the group consisting of a hydrogen atom, a fluorine atom, a cyano group, an alkyl group, a cycloalkyl group, an alkoxy group, a thioalkyl group, a silyl group, and an alkenyl group.

In the embodiment, the alkyl group is selected from the group consisting of a substituted or unsubstituted straight-chain alkyl group with the carbon number of 1 to 6, and a substituted or unsubstituted branched-chain alkyl group with the carbon number of 1 to 6. The cycloalkyl group is a substituted or unsubstituted cycloalkyl group with the carbon number of 1 to 6. The alkoxy group is selected from the group consisting of a substituted or unsubstituted straight-chain alkoxy group with the carbon number of 1 to 6, and a substituted or unsubstituted branched-chain alkoxy group with the carbon number of 1 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 1 to 6. The silyl group is selected from the group consisting of a substituted or unsubstituted straight-chain silyl group with the carbon number of 1 to 6, and a substituted or unsubstituted branched-chain silyl group with the carbon number of 1 to 6. The alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

A preferred example is the compound of Chemical Formula (1), o-CbzBz, where R9 is a benzimidazole group, and R1 to R8, R10 to R13 and R34 to R42 are all independent hydrogen atoms.

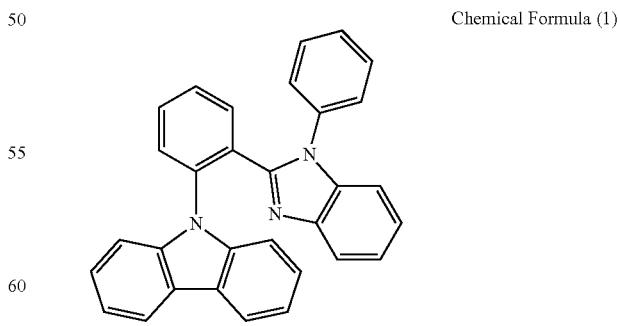

Chemical Formula (1)

Moreover, another preferred example is the compound of Chemical Formula (2), o-CbzDiBz, where R9 and R13 are both independent benzimidazole groups, and R1 to R8, R10 to R12 and R34 to R42 are all independent hydrogen atoms.

Chemical Formula (2)

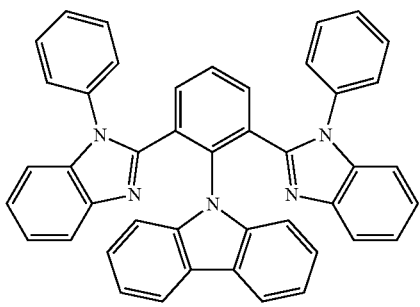

Alternatively, the host material can also be the above mentioned organic electroluminescent material which has a structure of the following General Formula (2).

General Formula (2)

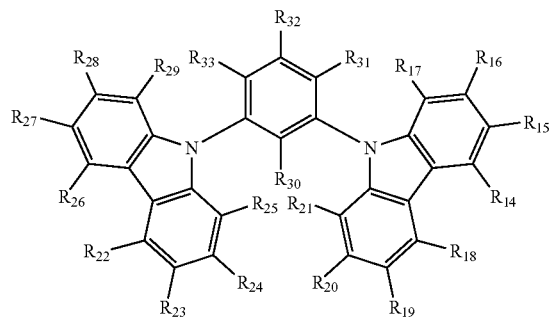

R30 is an independent benzimidazole derivative, and the benzimidazole derivative has the structure of the following General Formula (3).

General Formula (3)

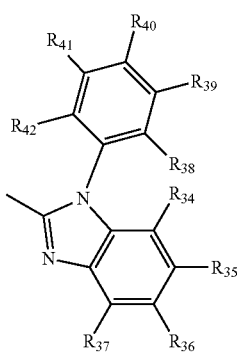

R14 to R29 and R31 to R42 are each independently selected from the group consisting of a hydrogen atom, a fluorine atom, a cyano group, an alkyl group, a cycloalkyl group, an alkoxy group, a thioalkyl group, a silyl group, and an alkenyl group.

In the embodiment, the alkyl group is selected from the group consisting of a substituted or unsubstituted straight-chain alkyl group with the carbon number of 1 to 6, and a substituted or unsubstituted branched-chain alkyl group with the carbon number of 1 to 6. The cycloalkyl group is a substituted or unsubstituted cycloalkyl group with the carbon number of 1 to 6. The alkoxy group is selected from the group consisting of a substituted or unsubstituted straight-chain alkoxy group with the carbon number of 1 to 6, and a substituted or unsubstituted branched-chain alkoxy group with the carbon number of 1 to 6. The thioalkyl group is selected from the group consisting of a substituted or unsubstituted straight-chain thioalkyl group with the carbon number of 1 to 6, and a substituted or unsubstituted branched-chain thioalkyl group with the carbon number of 1 to 6. The silyl group is selected from the group consisting of a substituted or unsubstituted straight-chain silyl group with the carbon number of 1 to 6, and a substituted or unsubstituted branched-chain silyl group with the carbon number of 1 to 6. The alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

A preferred example is the compound of Chemical Formula (3), o-DiCbzBz, where R14 to R29 and R31 to R42 are all independent hydrogen atoms.

Chemical Formula (3)

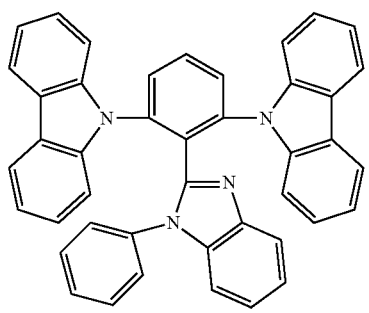

In one embodiment, the content of host material in organic luminescent layer is between 60 vol % to 95 vol %. Moreover, the content of guest material in organic luminescent layer is between 5 vol % to 40 vol %.

Furthermore, the guest materials may be any suitable luminescent materials applied to the organic luminescent layer of the organic electroluminescent device, for example but not limited to, $Ir(2-phq)_3$, $Ir(ppy)_3$, and FIrpic, and their structures are respectively shown as the following Chemical Formula (4), Chemical Formula (5), and Chemical Formula (6).

Chemical Formula (4)

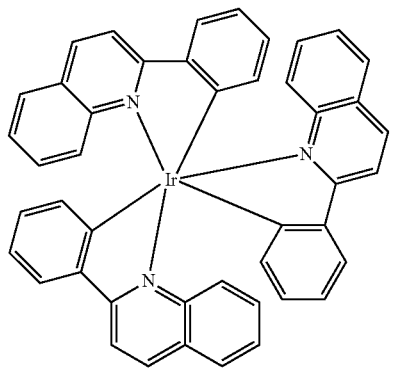

Chemical Formula (5)

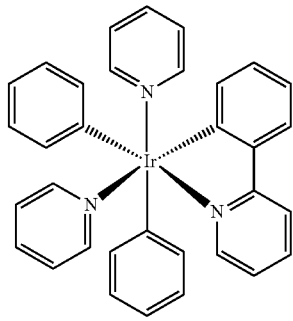

Chemical Formula (6)

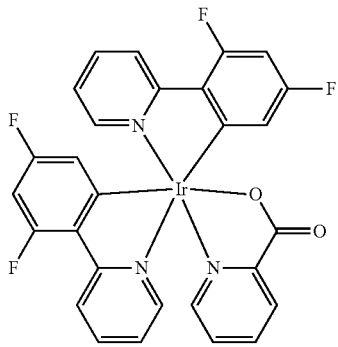

In addition, the material of the electron transport layer 168 may be, but not limited to, a metal complex, such as Tris-(8-hydroxy-quinoline)aluminum (Alq3) and bis(10-hydroxybenzo-[h]quinolinato)beryllium (BeBq2), or a heterocyclic compound, such as 2-(4-Biphenylyl)-5-(4-tert-butylphenyl)-1,3,4-oxadiazole (PBD), 3-(4-Biphenylyl)-4-phenyl-5-tert-butylphenyl-1,2,4-triazole (TAZ), 2,2',2"-(1,3,5-Benzinetriyl)-tris(1-phenyl-1-H-benzimidazole) (TPBI), diphenylbis(4-(pyridin-3-yl)phenyl)silane (DPPS), and 3,3'-[5'-[3-(3-Pyridinyl)phenyl][1,1':3',1"-terphenyl]-3,3"-diyl] bispyridine (TmPyPB). In the embodiment, the thickness of the electron transport layer 168 may be between 0.1 nm and 100 nm. The electron transport layer 168 may improve the velocity of the electron being transported from the second electrode layer 140 to the organic luminescent layer 166. Moreover, the material of the electron injection layer 169 may be, for example, LiF. The thickness of the electron injection layer 169 may be, for example, 0.9 nm.

Figure 2:
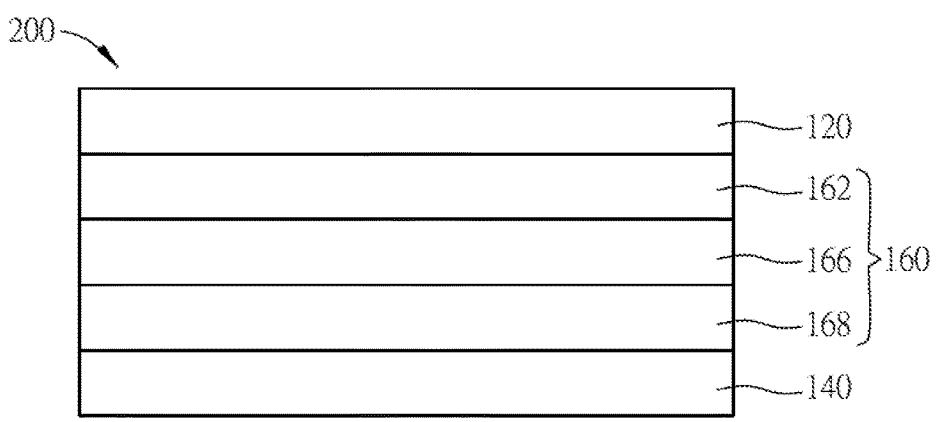
FIG. 2 is a schematic diagram of an organic electroluminescent device of the fourth embodiment according to the invention.

In addition, FIG. 2 is a schematic diagram of an organic electroluminescent device 200 of the fourth embodiment according to the invention. The configuration of the organic electroluminescent device 200 is substantially similar with that of the organic electroluminescent device 100, and same elements have substantial the same characteristics and functions. Therefore, the similar references relate to the similar elements, and detailed explanation is omitted hereinafter.

Please refer to FIG. 2, in the embodiment, the organic luminescent unit 160 can comprise a hole transport layer 162, organic luminescent layer 166, and electron transport layer 168. The organic luminescent layer 166 is disposed between the hole transport layer 162 and the electron transport layer 168.

Figure 3:
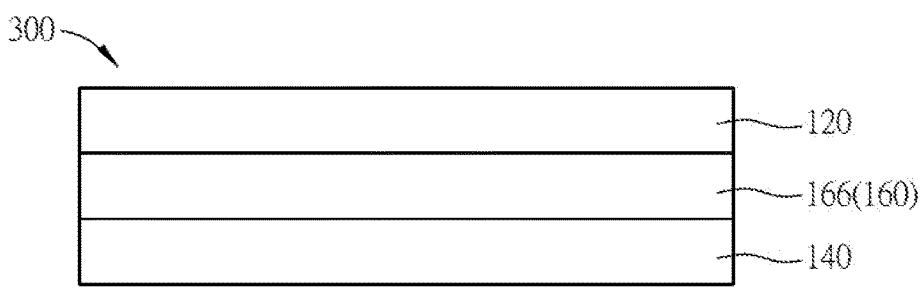
FIG. 3 is a schematic diagram of an organic electroluminescent device of the fifth embodiment according to the invention.

In addition, FIG. 3 is a schematic diagram of an organic electroluminescent device 300 of the fifth embodiment according to the invention. The configuration of the organic electroluminescent device 300 is substantially similar with that of the organic electroluminescent device 100, and same elements have substantial the same characteristics and functions. Therefore, the similar references relate to the similar elements, and detailed explanation is omitted hereinafter.

Please refer to FIG. 3, in the embodiment, the organic luminescent unit 160 can comprise an organic luminescent layer 166.

In addition, the configuration of the organic electroluminescent device according to the invention is not limited to what is disclosed in the third, fourth, or fifth embodiment. The third, fourth, and fifth embodiments are embodiments for illustration.

In order to illustrate the synthesis of Chemical Formula (1) to Chemical Formula (3), there are several examples shown below.

Example 1: Synthesis of Compound of Chemical Formula (1): o-CbzBz

2-Fluorobenzoyl chloride (4.75 g, 29.9 mmol) was dissolved in 30.0 mL dichloromethane (DCM) and was slowly added to a solution of triethylamine (TEA, 8.4 mL) and 2-aminodiphenylamine (6.08 g, 33.0 mmol) in 60 mL DCM. The mixture was stirred for 24 hours. The mixture was then washed with 1×100 mL $H_2O$ and 2×100 mL saturated $NaHCO_3$, and was neutralized with 0.5 N HCl. The organic layer was dried over anhydrous $MgSO_4$ and condensed to yield an intermediate. The intermediate was refluxed for 48 hours in 200 mL acetic acid to conduct cyclodehydration reaction. After the reaction, a crude reaction mixture was formed with a removal of solvent via vacuum distillation. The crude reaction mixture was dissolved in DCM and then was washed with NaOH (aq). The organic layer was collected, and was dried over anhydrous $MgSO_4$ to condense a crude product. The crude product was purified by a silica gel (chloroform:ethyl acetate=15:1) to yield compound 1 as white powder (6.15 g, 71%).

The melting point of compound 1 is 112-113° C. Spectral data as follow: $^1$H NMR (400 MHz, DMSO-$d_6$): δ 7.84-7.81 (m, 1H), 7.67 (td, $J_1$=7.44, $J_2$=1.68, 1H), 7.53-7.42 (m, 4H), 7.37-7.28 (m, 6H), 7.19 (td, $J_1$=8.92, $J_2$=0.72, 1H); $^{13}$C NMR (100 MHz, DMSO-$d_6$): δ 159.26 (d, $J_{CF}$=247.7), 147.87, 142.67, 135.92, 135.71 (d, $J_{CF}$=1.4), 132.45 (d, $J_{CF}$=2.3), 132.32 (d, $J_{CF}$=8.3), 129.64, 128.43, 126.44, 124.62 (d, $J_{CF}$=3.4), 123.66, 122.79, 119.62, 118.41 (d, $J_{CF}$=14.4), 115.79 (d, $J_{CF}$=21.1), 110.51; HRMS m/z [M+H]+ calcd 289.1141, obsd. 289.1105 Anal. calcd for $C_{19}H_{13}FN_2$: C, 79.15; H, 4.54; N, 9.72. Found: C, 79.05; H, 4.54; N, 9.56.

Next, cesium carbonate (4.89 g, 15.0 mmol), carbazole (1.76 g, 10.5 mmol) and white powder 1 (2.88 g, 9.99 mmol) were mixed in 12.5 mL dimethyl sulfoxide (DMSO, 0.25 M) and were heated up to 160° C. for 48 hours under argon atmosphere. After the reaction, the mixture was diluted with chloroform and was filtered through celite. The filtrate was washed twice with $NH_4Cl$ (aq) and 0.5 N NaOH (aq). The organic layer was collected, and was dried over anhydrous $MgSO_4$ to condense a crude solid. The crude solid was purified by recrystallization from methylene chloride and acetone to yield the compound of Chemical Formula (1) (o-CbzBz, 2.7 g, 62%). The compound of Chemical Formula (1) (o-CbzBz) was sublimed twice under thermal evaporation and deposition conditions before use.

The melting point of compound of Chemical Formula (1) (o-CbzBz) is 189-190° C. Spectral data as follow: $^1$H NMR (400 MHz, CDCl$_3$): δ 8.25-8.22 (m, 1H), 7.89 (d, J=7.6, 2H), 7.85 (d, J=8, 1H), 7.65-7.59 (m, 2H), 7.41-7.38 (m, 1H), 7.22 (td, $J_1$=7.6, $J_2$=0.8, 1H), 7.07-7.01 (m, 3H), 6.97 (td, $J_1$=8.2, $J_2$=1.2, 2H), 6.85-6.77 (m, 4H), 6.73 (t, J=8, 2H), 6.27 (d, J=7.2, 2H); $^{13}$C NMR (100 MHz, CDCl$_3$): δ 150.99, 142.96, 139.74, 136.26, 135.70, 134.74, 133.90, 131.10, 128.64, 128.33, 128.26, 127.80, 127.68, 125.56, 124.41, 123.49, 123.18, 122.67, 119.85, 119.68, 119.36, 110.23, 109.78; HRMS m/z [M+H]+ calcd 436.1814, obsd. 436.1815 Anal. calcd for C$_{31}$H$_{21}$N$_3$: C, 85.49; H, 4.86; N, 9.65. Found: C, 85.44; H, 4.91; N, 9.56.

Example 2: Synthesis of Compound of Chemical Formula (2): o-CbzDiBz 3.5 ml oxalyl chloride (40 mmol) and two drops of N,N-dimethylformamide (DMF) was added into a solution of 2-fluoroisophthalic acid (1.84 g, 10 mmol) in 40 ml DCM (0.25 M). The mixture was reacted at 50° C. for 4 hours, and then the solvent was removed to yield a yellowish crude reaction mixture. The crude reaction mixture was dissolved in 25 ml DCM and then was slowly added into a solution of triethylamine (5.62 mL) and 2-aminodiphenylamine (3.87 g, 21 mmol) in 25 ml DCM. After 24 hours reaction, a large amount of precipitates was formed. The precipitates were washed with methanol and were collected by suction filtration. The crude reaction mixture was refluxed for 48 hours in 250 mL acetic acid. The solvent was removed by vacuum distillation to a crude product. The crude product was dissolved in DCM and was washed with NaOH (aq). The organic layer was collected, dried over and condensed by anhydrous MgSO$_4$ and washed with toluene to yield a compound 2 as white solid (3.46 g, 72%).

The melting point of compound 2 is 297-298° C. Spectral data as follow: $^1$H NMR (400 MHz, CDCl$_3$): δ 8.25 (d, J=7.6, 2H), 7.84 (t, J=8, 1H), 7.72 (d, J=8.4, 2H), 7.59 (d, J=7.6, 2H), 7.13 (td, J$_1$=8, J$_2$=0.8, 2H), 6.94 (td, J$_1$=7.6, J$_2$=8, 2H), 6.75-6.65 (m, 6H), 6.57 (br, 4H), 6.48 (td, J$_1$=8, J$_2$=1.2, 2H), 6.24 (d, J=8.4, 2H), 6.06 (br, 4H); $^{13}$C NMR (100 MHz, CDCl$_3$): δ 150.46, 142.69, 138.13, 138.88, 135.19, 134.39, 133.89, 130.10, 128.43, 128.13, 127.73, 125.10, 123.95, 123.09, 123.05, 122.54, 119.49, 119.43, 118.03, 110.09, 110.03; HRMS m/z [M+H]$^+$ calcd 628.2501, obsd. 628.2490. Anal. Calcd for C$_{44}$H$_{29}$N$_5$: C, 84.19; H, 4.66; N, 11.16. Found: C, 84.10; H, 4.72; N, 11.07.

Next, cesium carbonate (2.4 g, 7.5 mmol), carbazole (0.88 g, 5.25 mmol) and compound 2 as white solid (2.4 g, 5 mmol) were mixed in 6.25 mL N-methylpyrrolidone (NMP, 0.8 M) and were heated up to 200° C. for 48 hours under argon atmosphere. After cooling down to room temperature, the mixture was diluted by NMP and was poured into water. Participates were collected and purified by a silica gel column (from chloroform to chloroform:ethyl acetate=5:1) to yield a compound of Chemical Formula (2) (o-CbzDiBz) as white powder (2.2 g, 70%).

The melting point of the compound of Chemical Formula (2) (o-CbzDiBz) is 297-298° C. Spectral data as follow: $^1$H NMR (400 MHz, CDCl$_3$): δ 8.25 (d, J=7.6, 2H), 7.84 (t, J=8, 1H), 7.72 (d, J=8.4, 2H), 7.59 (d, J=7.6, 2H), 7.13 (td, J$_1$=8, J$_2$=0.8, 2H), 6.94 (td, J$_1$=7.6, J$_2$=8, 2H), 6.75-6.65 (m, 6H), 6.57 (br, 4H), 6.48 (td, J$_1$=8, J$_2$=1.2, 2H), 6.24 (d, J=8.4, 2H), 6.06 (br, 4H); $^{13}$C NMR (100 MHz, CDCl$_3$): δ 150.46, 142.69, 138.13, 138.88, 135.19, 134.39, 133.89, 130.10, 128.43, 128.13, 127.73, 125.10, 123.95, 123.09, 123.05, 122.54, 119.49, 119.43, 118.03, 110.09, 110.03; HRMS m/z [M+H]$^+$ calcd 628.2501, obsd. 628.2490. Anal. Calcd for C$_{44}$H$_{29}$N$_5$: C, 84.19; H, 4.66; N, 11.16. Found: C, 84.10; H, 4.72; N, 11.07.

Example 3: Synthesis of Compound of Chemical Formula (3): o-DiCbzBz 2,6-Difluorobenzoyl chloride (5.3 g, 30.0 mmol) was dissolved in 30 mL DCM and added slowly to a solution of triethylamine (8.4 mL) and 2-aminodiphenylamine (6.08 g, 33.0 mmol) in 60 mL DCM. After 24 h, the mixture was then washed with 1×100 mL H$_2$O and 2×100 mL saturated NaHCO$_3$, and was neutralized with 0.5 N HCl. The organic layer was dried over anhydrous MgSO$_4$ and condensed to yield an intermediate. The intermediate was refluxed for 48 hours in 200 mL acetic acid to conduct dehydration reaction. After the reaction, a crude reaction mixture was formed with a removal of solvent via vacuum distillation. The crude reaction mixture was dissolved in DCM and then was washed with NaOH (aq). The organic layer was collected, dried over and condensed by anhydrous MgSO$_4$, and purified by a silica gel column (chloroform) to yield a compound 3 as white powder (7.16 g, 78%).

The melting point of the compound 3 is 203-204° C. Spectral data as follow: $^1$H NMR (400 MHz, CDCl$_3$): δ 7.92 (d, J=7.76, 1H), 7.41-7.27 (m, 9H), 6.90-6.86 (m, 2H); $^{13}$C NMR (100 MHz, CDCl$_3$): δ 160.33 (dd, J$_{CF}$=251.1), 142.55, 141.99, 135.46, 135.05, 131.53 (t, J$_{CF}$=10.2), 128.87, 127.97, 125.79, 123.21, 122.35, 119.75, 111.04, 110.79, 109.92; HRMS m/z [M+H]$^+$ calcd 307.1047, obsd. 307.1011 Anal. calcd for C$_{19}$H$_{12}$F$_2$N$_2$: C, 74.50; H, 3.95; N, 9.15. Found: C, 74.43; H, 3.85; N, 9.14.

Next, cesium carbonate (9.77 g, 30.0 mmol), carbazole (3.43 g, 20.5 mmol) and white powder 3 (3.06 g, 10 mmol) were mixed in 25 mL DMSO (0.4 M) and were heated up to 160° C. for 48 hours under argon atmosphere. After the reaction, the mixture was diluted with chloroform and was filtered through celite. The filtrate was washed twice with NH$_4$Cl (aq) and 0.5 N NaOH (aq). The organic layer was dried over anhydrous MgSO$_4$ to condense a crude solid. The crude solid was washed with methanol/ether to yield o-DiCbzBz. The o-DiCbzBz was purified and recrystallized from DCM/EtOH to yield an essentially pure compound of Chemical Formula (3) (o-DiCbzBz, 5.38 g, 90%). The compound of Chemical Formula (3) (o-DiCbzBz) was sublimed twice under thermal evaporation and deposition conditions before use.

The melting point of the compound of Chemical Formula (3) (o-DiCbzBz) is 295-296° C. Spectral data as follow: $^1$H NMR (400 MHz, CD$_2$Cl$_2$): δ 8.01 (d, J=8, 4H), 7.81 (t, J=8, 1H), 7.67 (d, J=8.4, 2H), 7.61 (d, J=7.6, 2H), 7.39 (td, J$_1$=7.8, J$_2$=1.2, 2H), 7.25-7.15 (m, 7H), 7.03 (t, J=7.6, 1H), 6.94-6.88 (m, 5H), 6.84 (td, J$_1$=7.4, J$_2$=1.2, 1H), 6.63 (d, J=8, 1H), 6.44 (d, J=7.2, 2H); $^{13}$C NMR (100 MHz, CD$_2$Cl$_2$): δ 146.20, 142.93, 142.48, 142.22, 140.78, 135.81, 135.25, 132.65, 130.82, 130.63, 129.44, 128.55, 126.23, 125.99, 125.91, 124.46, 123.81, 123.45, 122.53, 120.58, 120.49, 120.04, 119.86, 112.68, 110.58, 110.37; HRMS m/z [M+H]$^+$ calcd 601.2392, obsd. 601.2403 Anal. calcd for C$_{43}$H$_{28}$N$_4$: C, 85.98; H, 4.70; N, 9.33. Found: C, 85.71; H, 4.75; N, 9.28.

Evaluation Methods for the Host Material

The host material includes the compound which is mentioned above from Example 1 to Example 3 (i.e., Chemical Formula (1) to Chemical Formula (3)). The evaluation methods for the host material is to perform the measurements of the triplet energy gap (E$_T$), the glass transition temperature (T$_g$), the pyrolysis temperature (T$_d$), the highest occupied molecular orbital energy gap (HOMO), and the lowest unoccupied molecular orbital energy gap (LUMO) on above mentioned compound of examples, respectively. The triplet energy gap measured at low temperature by spectrometer is the basis of selecting the host material of phosphorescent luminary. For blue light-emitting diode, FIrpic ($E_T$=2.65 eV) is a common phosphorescent luminary and the $E_T$ of the host luminary developed by FIrpic should be higher than 2.65 eV to avoid back energy transfer reducing the spectrometer. The glass transition temperature and the pyrolysis temperature respectively measured by differential scanning calorimeter (DSC) and thermogravimetric analyzer (TGA) is considered to be the basis of the stability for the fabrication and performance of unit. HOMO and LUMO are acquired receptively from oxidation potential and reduction potential of the material by using cyclic voltammetry, which can facilitate in searching of an electron injection material with small difference energy gap and enhance the efficiency of the unit. The properties of the compounds of Chemical Formula (1) (o-CbzBz), Chemical Formula (2) (o-CbzDiBz), and Chemical Formula (3) (o-DiCbzBz) are shown in Table 1.

TABLE 1

| Compound | $E_T$ (eV) | $T_g$ (° C.) | $T_d$ (° C.) | HOMO (eV) | LUMO (eV) |
|---|---|---|---|---|---|
| Chemical Formula (1) | 2.90 | 77 | 323 | −5.7 | −2.1 |
| Chemical Formula (2) | 2.91 | 132 | 370 | −5.7 | −2.2 |
| Chemical Formula (3) | 3.10 | 117 | 381 | −5.7 | −2.2 |

According to Table 1, the pyrolysis temperatures of the compound of Chemical Formula (1) (o-CbzBz), Chemical Formula (2) (o-CbzDiBz) and Chemical Formula (3) (o-DiCbzBz) are all higher than 300° C. It is because that their structures contain multiple benzene rings which are rigid structures, so that the pyrolysis caused by the heat is not easily occurred during the heating process. Based on the reason mentioned above, their derivatives have fine heat stability and high triplet energy gap and are quite beneficial to be the host material in organic luminescent layer of organic light emitting diode.

The Efficiency of Compound (Chemical Formula (1), o-CbzBz, Chemical Formula (2), o-CbzDiBz, and Chemical Formula (3), o-DiCbzBz) which were Used as Host Material in Organic Light Emitting Diode The unit structure is ITO/TAPC (50 nm)/mCP (10 nm)/host: emitter (30 nm)/DPPS (30 nm)/LiF (0.9 nm)/Al (120 nm). The host materials of the organic luminescent layer are based on the compound of Chemical Formula (1), Chemical Formula (2) or Chemical Formula (3). The host materials were mixed with the guest material at various ratio of emitter (FIrpic). Here, the material of first electrode layer of the organic electroluminescent device is ITO. The material of the second electrode layer is aluminum with the thickness of 120 nm. The material of the hole transport layer is TAPC with the thickness of 50 nm. The thickness of the organic luminescent layer is 30 nm. The material of the electron blocking layer is mCP with the thickness of 10 nm. The material of the electron transport layer is DPPS with the thickness of 30 nm. The material of electron injecting layer is LiF with the thickness of 0.9 nm. The organic electroluminescent devices are made by vapor deposition to form the above-mentioned layers, and the driving voltage (V) under the luminance of 1000 cd/m², the maximum current efficiency (cd/A), the maximum power efficiency (lm/W), and the maximum external quantum efficiency (EQE) (%) of the organic electroluminescent devices are measured. The results are shown in Table 2.

TABLE 2

| unit[a] | driving voltage (V)[b] | maximum current efficiency (cd/A) | maximum power efficiency (lm/W) | EQE (%) |
|---|---|---|---|---|
| Chemical Formula (1) −12% | 5.65 | 47.8@4 V | 42.4@3.5 V | 22.57 |
| Chemical Formula (2) −12% | 5.38 | 48.88@4 V | 47.58@3 V | 23.14 |
| Chemical Formula (3) −6% | 6.05 | 57.5@4.5 V | 48.9@3.5 V | 27.00 |

[a]The doping concentration of FIrpic
[b]the unit of operation voltage under the luminance of 1000 cd/m²

The organic electroluminescent devices shown in Table 2 not only have low driving voltages but also have the fine current efficiency, power efficiency and external quantum efficiency. Accordingly, the host materials of the present invention have high transmission rate of electrons and holes, and are not necessarily to be operated under high driving voltage. Also, the external quantum efficiencies of the host materials shown in Table 2 are high as well. Consequently, the host materials of the present invention have higher triplet energy gap, which is beneficial to reduce back energy transfer and to increase the luminous efficiency of organic electroluminescent device.

In summary, as mentioned above, the organic electroluminescent material containing benzimidazole and the organic electroluminescent device according to the present invention is based on the structure of N-phenylcarbazole (NPC) and 1,3-Bis(N-carbazolyl)benzene (mCP) and in ortho-substitution with various number of electron-transporting benzimidazoles. Accordingly, the host materials with bipolar property, such as o-CbzBz, o-CbzDiBz and o-DiCbzBz, are formed. In the present invention, it utilizes the benzimidazole group to be electron-transporting group and the carbazole group to be hole-transporting group, whereas the carbazole group is undergone single ortho-substituted benzene ring modification, to synthesize a phosphorescent bipolar host material. Therefore, such phosphorescent bipolar host material and the organic light-emitting diode comprising such material will have high luminous efficiency.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An organic electroluminescent material, comprising a structure of the following General Formula (2), General Formula (2)

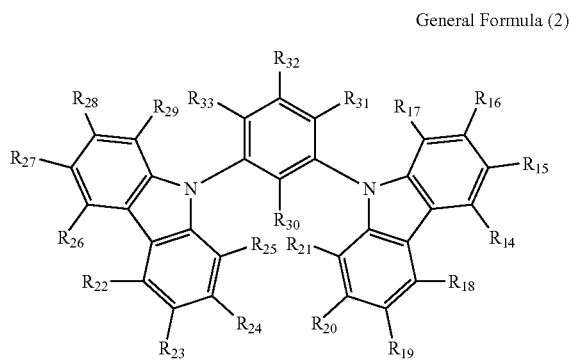

Wherein $R_{30}$ is an independent benzimidazole derivative, the benzimidazole derivative have the structure of the following General Formula (3), and General Formula (3)

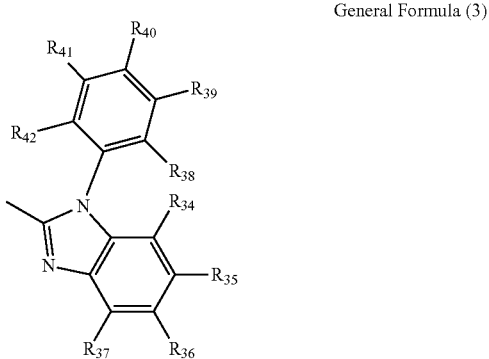

Wherein $R_{14}$ to $R_{29}$ and $R_{31}$ to $R_{42}$ are each independently selected from the group consisting of a hydrogen atom, a fluorine atom, a cyano group, an alkyl group, a cycloalkyl group, an alkoxy group, a thioalkyl group, a silyl group, and an alkenyl group.

2. The organic electroluminescent material of claim 1, wherein the alkyl group is selected from the group consisting of a substituted or unsubstituted straight-chain alkyl group with the carbon number of 1 to 6, and a substituted or unsubstituted branched-chain alkyl group with the carbon number of 1 to 6, the cycloalkyl group is a substituted or unsubstituted cycloalkyl group with the carbon number of 1 to 6, the alkoxy group is selected from the group consisting of a substituted or unsubstituted straight-chain alkoxy group with the carbon number of 1 to 6, and a substituted or unsubstituted branched-chain alkoxy group with the carbon number of 1 to 6, thioalkyl group is selected from the group consisting of a substituted or unsubstituted straight-chain thioalkyl group with the carbon number of 1 to 6, a substituted or unsubstituted branched-chain thioalkyl group with the carbon number of 1 to 6, the silyl group is selected from the group consisting of a substituted or unsubstituted straight-chain silyl group with the carbon number of 1 to 6, and a substituted or unsubstituted branched-chain silyl group with the carbon number of 1 to 6, and the alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

3. An organic electroluminescent device, comprising:
a first electrode layer;
a second electrode layer; and
an organic luminescent unit, disposed between the first electrode layer and the second electrode layer, wherein the organic luminescent unit has at least an organic luminescent material as shown in General Formula (2), General Formula (2)

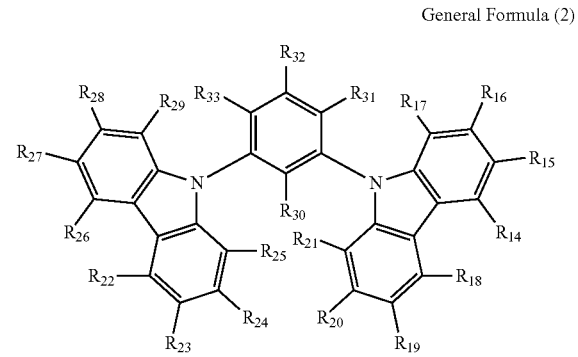

wherein $R_{30}$ is an independent benzimidazole derivatives, and the benzimidazole derivatives have the structures of the following General Formula (3), General Formula (3)

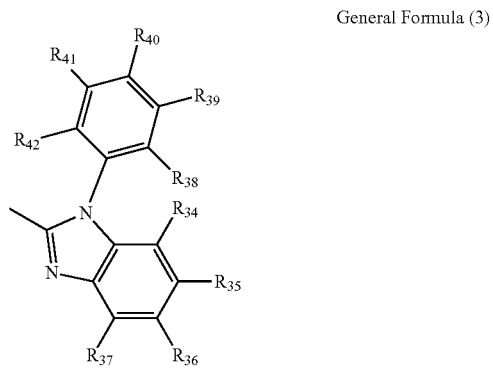

wherein $R_{14}$ to $R_{29}$ and $R_{31}$ to $R_{42}$ are each independently selected from the group consisting of a hydrogen atom, a fluorine atom, a cyano group, an alkyl group, a cycloalkyl group, an alkoxy group, a thioalkyl group, a silyl group, and an alkenyl group.

4. The organic electroluminescent device of claim 3, wherein the alkyl group is selected from the group consisting of a substituted or unsubstituted straight-chain alkyl group with the carbon number of 1 to 6, and a substituted or unsubstituted branched-chain alkyl group with the carbon number of 1 to 6, the cycloalkyl group is a substituted or unsubstituted cycloalkyl group with the carbon number of 1 to 6, the alkoxy group is selected from the group consisting of a substituted or unsubstituted straight-chain alkoxy group with the carbon number of 1 to 6, and a substituted or unsubstituted branched-chain alkoxy group with the carbon number of 1 to 6, thioalkyl group is selected from the group consisting of a substituted or unsubstituted straight-chain thioalkyl group with the carbon number of 1 to 6, a substituted or unsubstituted branched-chain thioalkyl group with the carbon number of 1 to 6, the silyl group is selected from the group consisting of a substituted or unsubstituted straight-chain silyl group with the carbon number of 1 to 6, and a substituted or unsubstituted branched-chain silyl group with the carbon number of 1 to 6, and the alkenyl group is selected from the group consisting of a substituted or unsubstituted straight-chain alkenyl group with the carbon number of 1 to 6, and a substituted or unsubstituted branched-chain alkenyl group with the carbon number of 1 to 6.

5. The organic electroluminescent device of claim 3, wherein the organic luminescent unit comprises an organic luminescent layer.

6. The organic electroluminescent device of claim 5, wherein the organic luminescent unit further comprises a hole transport layer and an electron transport layer, and the organic luminescent layer is disposed between the hole transport layer and the electron transport layer.

7. The organic electroluminescent device of claim 5, wherein the organic electroluminescent unit further comprises a hole transport layer, an electron blocking layer, an electron transport layer and an electron injection layer, and the electron blocking layer, the organic luminescent layer and the electron transport layer are sequentially disposed between the hole transport layer and the electron injection layer.

8. The organic electroluminescent device of claim 5, wherein the organic luminescent layer comprises a host material and a guest material, and the host material is the organic luminescent material and the guest material is a phosphorescent material.

9. The organic electroluminescent device of claim 8, wherein the content of the host material in the organic luminescent layer is between 60 vol % to 95 vol %.

10. The organic electroluminescent device of claim 8, wherein the content of the guest material in the organic luminescent layer is between 5 vol % to 40 vol %.

* * * * *